(12) United States Patent
Lai et al.

(10) Patent No.: US 7,367,800 B2
(45) Date of Patent: May 6, 2008

(54) PRE-TORQUED ORTHODONTIC APPLIANCE WITH ARCHWIRE RETAINING LATCH

(75) Inventors: Ming-Lai Lai, Arcadia, CA (US);
Jirina V. Pospisil, Hacienda Heights, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 209 days.

(21) Appl. No.: 11/050,615

(22) Filed: Feb. 2, 2005

(65) Prior Publication Data

US 2006/0172249 A1    Aug. 3, 2006

(51) Int. Cl.
*A61C 3/00* (2006.01)

(52) U.S. Cl. .................................. 433/11; 433/8; 433/9

(58) Field of Classification Search .................. 433/11, 433/8, 9
See application file for complete search history.

(56) References Cited

U.S. PATENT DOCUMENTS

| | | |
|---|---|---|
| 1,991,047 A | 2/1935 | Boyd et al. |
| 3,084,437 A | 4/1963 | Neger |
| 3,327,393 A | 6/1967 | Brader |
| 3,772,787 A | 11/1973 | Hanson |
| 3,871,096 A | 3/1975 | Wallshein |
| 4,248,588 A | 2/1981 | Hanson |
| 4,492,573 A | 1/1985 | Hanson |
| 4,698,017 A | 10/1987 | Hanson |
| 4,725,229 A | 2/1988 | Miller |
| 4,954,080 A | 9/1990 | Kelly et al. |
| 5,039,302 A | 8/1991 | Keys |
| 5,094,614 A | 3/1992 | Wildman |
| 5,356,289 A | 10/1994 | Watanabe |
| 5,466,151 A | 11/1995 | Damon |
| 5,474,445 A | 12/1995 | Voudouris |
| 5,516,284 A | 5/1996 | Wildman |
| 5,562,444 A | 10/1996 | Heiser et al. |
| 5,613,850 A | 3/1997 | Wildman et al. |
| 5,630,715 A | 5/1997 | Voudouris |
| 5,630,716 A | 5/1997 | Hanson |
| 5,685,711 A | 11/1997 | Hanson |
| 5,711,666 A | 1/1998 | Hanson |
| 5,857,849 A | 1/1999 | Kurz |
| 5,857,850 A | 1/1999 | Voudouris |
| 5,863,199 A | 1/1999 | Wildman |

(Continued)

FOREIGN PATENT DOCUMENTS

WO    WO 01/22901    4/2001

(Continued)

OTHER PUBLICATIONS

Pending U.S. Appl. No. 10/900,888, filed Jul. 28, 2004.

*Primary Examiner*—Cris Rodriguez
*Assistant Examiner*—Candice C Stokes
(74) *Attorney, Agent, or Firm*—James D. Christoff

(57) ABSTRACT

An orthodontic appliance such as a bracket or buccal tube has a latch for retaining an archwire in an archwire slot. The appliance also includes built-torque in order to reduce the need for the practitioner to manually bend the archwire by twisting the archwire about its longitudinal axis during the course of treatment. The latch comprises at least one clip having certain features that significantly reduce strain during opening movements of the clip. As a result, the fatigue life of the clip is enhanced.

14 Claims, 2 Drawing Sheets

U.S. PATENT DOCUMENTS

| | | |
|---|---|---|
| 5,890,893 A | 4/1999 | Heiser |
| 5,908,293 A | 6/1999 | Voudouris |
| 6,554,612 B2 | 4/2003 | Georgakis et al. |
| 6,648,638 B2 | 11/2003 | Castro et al. |
| 6,984,127 B2 * | 1/2006 | Lai ............................... 433/8 |
| 2004/0086825 A1 | 5/2004 | Lai et al. |
| 2004/0166459 A1 | 8/2004 | Voudouris |
| 2005/0123875 A1 | 6/2005 | Stadtmiller et al. |

FOREIGN PATENT DOCUMENTS

| | | |
|---|---|---|
| WO | WO 02/089693 | 11/2002 |
| WO | WO 2005/044132 | 5/2005 |

* cited by examiner

PRE-TORQUED ORTHODONTIC APPLIANCE WITH ARCHWIRE RETAINING LATCH

BACKGROUND OF THE INVENTION

1. Field of the Invention

This invention broadly relates to appliances that are used during the course of orthodontic treatment. More particularly, the present invention relates to orthodontic appliances that are provided with built-in torque as well as a latch for releasably retaining an archwire in an archwire slot of the appliance.

2. Description of the Related Art

Orthodontic therapy is a specialized type of treatment within the field of dentistry, and involves movement of malpositioned teeth to improved locations along the dental arches. Orthodontic treatment often enhances the patient's facial appearance, especially in regions near the front of the oral cavity. Orthodontic treatment can also improve the patient's occlusion so that the teeth function better with each other during mastication.

Many types of orthodontic treatment programs involve the use of a set of tiny appliances and archwires that are commonly known collectively as "braces". During such treatment programs, small appliances known as brackets are fixed to the patient's anterior, cuspid and bicuspid teeth, and an archwire is inserted into a slot of each bracket. The archwire forms a track to guide movement of the teeth to orthodontically correct locations. End sections of the archwires are often captured in tiny appliances known as buccal tubes that are fixed to the patient's molar teeth.

Many orthodontic brackets have small wings known as "tiewings" that are connected to a body of the bracket. Once the bracket has been attached to a tooth and an archwire has been placed in the archwire slot of the bracket, a ligature is coupled to the bracket in order to retain the archwire in the archwire slot. One common type of commercially available orthodontic ligatures is a small, elastomeric O-ring that is installed by stretching the O-ring along a path behind the tiewings and over the facial side of the archwire.

Certain types of orthodontic brackets are known as self-ligating brackets, and are provided with a latch for coupling the archwire to the bracket. Use of the latch avoids the need to use a ligature to couple the archwire to the bracket. The latch may comprise a movable clip, spring member, cover, shutter, bale or other structure that is connected to the bracket body for retaining the archwire in the archwire slot.

Improved, self-ligating orthodontic brackets are described in applicant's published PCT applications entitled "ORTHODONTIC APPLIANCE WITH SELF-RELEASING LATCH", Nos. WO01/22901 and WO02/089693. The appliances described in those applications have a latch for retaining an archwire in the archwire slot, and the latch releases the archwire from the archwire slot whenever the archwire exerts a force on the appliance that exceeds a certain minimum value. The minimum value is significantly less than the force required in the same direction to debond the appliance from the tooth, and consequently helps ensure that the appliance will not spontaneously debond from the tooth during the course of treatment.

Many orthodontic appliances have an archwire slot that has a rectangular cross-sectional configuration when viewed in reference planes perpendicular to the longitudinal axis of the archwire slot. When an archwire having a matching rectangular cross-sectional configuration is placed in the archwire slot, the sides of the archwire can exert in certain situations a pivotal force on the appliance in directions along an arc about the longitudinal axis of the archwire. This pivotal force is commonly referred to as "torque" and serves to pivot the associated tooth in a corresponding direction as may be desired. For example, the practitioner may exert torque on a somewhat inclined upper front tooth in order to move the tooth toward a more upright orientation.

One common orthodontic treatment technique is known as the "straight wire technique". In this technique, brackets and buccal tubes are selected and placed at certain locations on the teeth so that the curved archwire is level and extends in a flat reference plane at the conclusion of treatment. Use of the straight wire technique often obviates the need for the practitioner to place bends or twists in the archwire, resulting in a savings of time for both the practitioner and the patient.

Certain orthodontic appliances with rectangular archwire slots are provided with "built-in torque" or "pre-applied torque". In those appliances, the sides of the archwire slots are oriented at a certain angle with respect to the base of the appliance. The angle is selected according to the desired angular orientation of the tooth at the end of treatment such that the top and bottom sides of the archwire slot lie in corresponding reference planes that also contain the top and bottom sides of archwire slots of other appliances in the same dental arch. As a result, the practitioner using the straight wire technique need not place a twist in the archwire in order to move the adjacent tooth to its desired angular inclination.

Self-ligating orthodontic appliances having a latch with one or more clips such as the clips described in the PCT applications mentioned above may be provided with built-in torque as described in the preceding paragraphs. It is desirable for such pre-torqued, self-ligating appliances to be as small as possible in order to minimize patient discomfort and undue contact with oral tissue. However, it is also important to ensure that the latch reliably opens and closes as intended over extended periods of time and does not fracture during use.

SUMMARY OF THE INVENTION

The present invention is directed toward improvements in self-ligating orthodontic appliances, including improvements in latches for self-ligating orthodontic appliances. In one aspect of the invention, the appliances include an improved latch that comprises one or more clips. The clips have a certain construction that is especially advantageous for use with pre-torqued appliances. The clips have certain features that help assure that the clip will reliably and consistently open and close a number of times during the expected course of treatment.

In more detail, the present invention in one aspect is directed to a clip for releasably retaining an archwire in an archwire slot of an orthodontic appliance. The clip comprises a first section and a second section opposed to the first section. The first section and the second section extend in generally parallel directions and are spaced apart from each other to present a region for receiving an archwire. The clip also includes a third section having a longitudinal axis extending in a direction generally perpendicular to the direction of extension of the first section and the second section. The clip further includes a first corner portion that interconnects the first section and the third section, and a second corner portion that interconnects the second section and the third section. The first corner portion extends in a direction away from the first section a certain distance, and the second corner portion extends in a direction away from the second section a distance that is greater than the certain distance. The third section has a configuration that is generally symmetrical about a reference axis perpendicular to the longitudinal axis of the third section when viewed in a reference plane containing the first section, the second section and the third section.

The present invention is also directed in another aspect to an orthodontic appliance. The appliance includes a base and a body extending outwardly from the base, and the body includes a wall section extending in a direction generally along a mesial-distal reference axis. The appliance further includes an archwire slot that extends across the body in a generally mesial-distal direction, and a clip for releasably retaining an archwire in the archwire slot. The clip includes a first section and a second section opposed to the first section. The first section and the second section extend in generally parallel directions and are spaced apart from each other to present a region for receiving an archwire. The clip further includes a third section having a longitudinal axis extending in a direction generally perpendicular to the direction of extension of the first section and the second section. The clip also includes a first corner portion interconnecting the first section and the third section, and a second corner portion interconnecting the second section and the third section. The first corner portion extends in a direction away from the first section a certain distance, and the second corner portion extends in a direction away from the second section a distance that is greater than the certain distance. The third section has a configuration that is generally symmetrical about a reference axis perpendicular to the longitudinal axis of the third section when viewed in a reference plane containing the first section, the second section and the third section. The first corner portion and the second corner portion are in contact with the wall section of the body.

Other aspects of the invention are described in the paragraphs that follow and are illustrated in the accompanying drawings.

Definitions

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Buccolabial" means in a direction toward the patient's cheeks or lips.

"Lingual" means in a direction toward the patient's tongue.

DETAILED DESCRIPTION OF THE PREFERRED EMBODIMENTS

Figure 1:
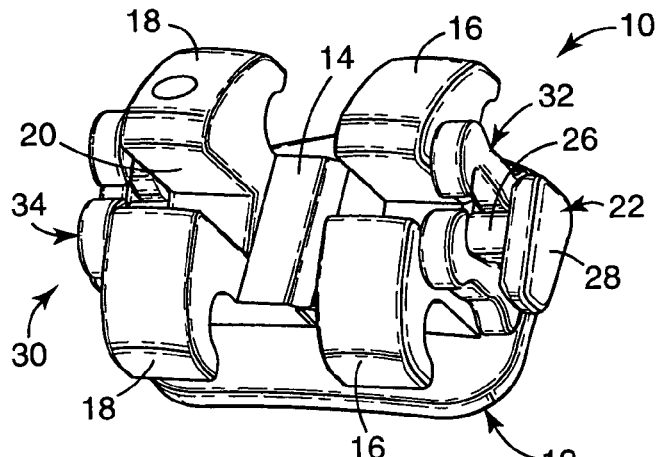
FIG. 1 is a perspective view of an orthodontic appliance having a latch that is constructed in accordance with one embodiment of the present invention.
Figure 2:
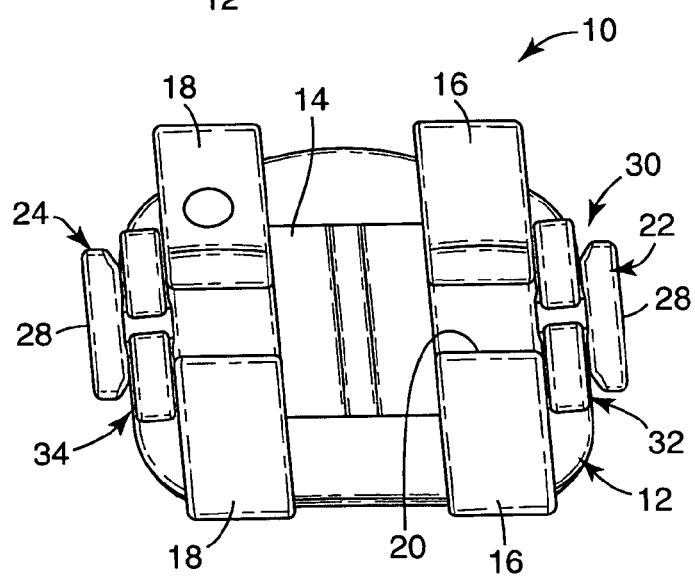
FIG. 2 is a front elevational view of the appliance shown in FIG. 1, looking in a lingual direction toward a buccolabial side of the appliance.
Figure 3:
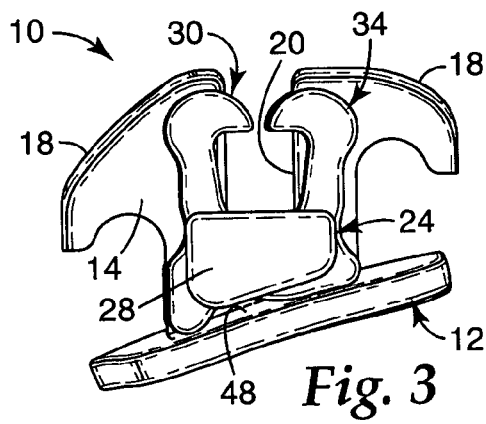
FIG. 3 is a side elevational view looking in a mesial direction toward a mesial side of the appliance illustrated in FIGS. 1 and 2.

An orthodontic appliance constructed in accordance with one embodiment of the present invention is illustrated in FIGS. 1-3 and is broadly designated by the numeral 10. In this embodiment, the appliance 10 is an orthodontic bracket adapted to be secured to the buccolabial surface of a patient's tooth. Alternatively, the appliance could be a molar appliance, a lingual appliance, or any other orthodontic appliance that is adapted to receive an archwire for controlling movement of the associated tooth during the course of orthodontic treatment.

The appliance 10 includes a base 12 for bonding the appliance directly to the patient's tooth enamel by the use of an adhesive. Preferably, the base 12 has an outwardly-facing lingual surface with a concave compound contour that matches the convex compound contour of the patient's tooth surface. Optionally, the lingual surface of the base 12 may be provided with grooves, particles, recesses, undercuts, a chemical bond enhancement material or any other material or structure or any combination of the foregoing that facilitates bonding the appliance 10 directly to the patient's tooth surface.

A body 14 of the appliance 10 extends outwardly from the base 12 in a generally buccolabial direction. The body 14 in this embodiment includes a spaced-apart pair of mesial tiewings 16 and a pair of spaced-apart distal tiewings 18. An archwire slot 20 extends across the body 14 in a generally mesial-distal direction and along the space presented between the pair of mesial tiewings 16 and along the space presented between the pair of distal tiewings 18. Optionally, one or more of the tiewings 16, 18 may be omitted if desired.

The appliance 10 also includes a mesial support 22 that extends outwardly from the body 14 in a mesial direction, and a distal support 24 that extends outwardly from the body 14 in a distal direction. Each of the supports 22, 24 includes a neck 26 (see, e.g., FIG. 1) and an outermost flange or head 28. Optionally, the supports 22, 24 are integrally connected to the body 14. As another option, the supports 22, 24 may be affixed to the body 14 after first being separately manufactured.

As another option, the supports 22, 24 may comprise opposite, outer end portions of an archwire slot liner that is affixed to the body 14. Suitable examples of archwire slot liners are described in pending U.S. patent applications Ser. No. 10/900,888 entitled "SELF-LIGATING ORTHODONTIC APPLIANCE WITH POST FOR CONNECTION TO A LATCH", filed Jul. 28, 2004 and Ser. No. 10/730,344 entitled "CERAMIC ORTHODONTIC APPLIANCE WITH ARCHWIRE SLOT LINER", filed Dec. 8, 2003. Preferably, the archwire slot liners are made of a metallic material in instances where the body 14 is made of a plastic or ceramic material, such as the ceramic materials described in U.S. Pat. Nos. 4,954,080 and 6,648,638.

The appliance 10 also includes a latch 30 that is connected to the body 14 for releasably retaining an archwire in the archwire slot 20. In the illustrated embodiment, the latch 30 includes a mesial clip 32 and a distal clip 34 although other constructions are also possible. For example, the latch 30 could have only a single clip that is optionally located in the space between the pair of mesial tiewings 16 and the pair of distal tiewings 18.

Figure 4:
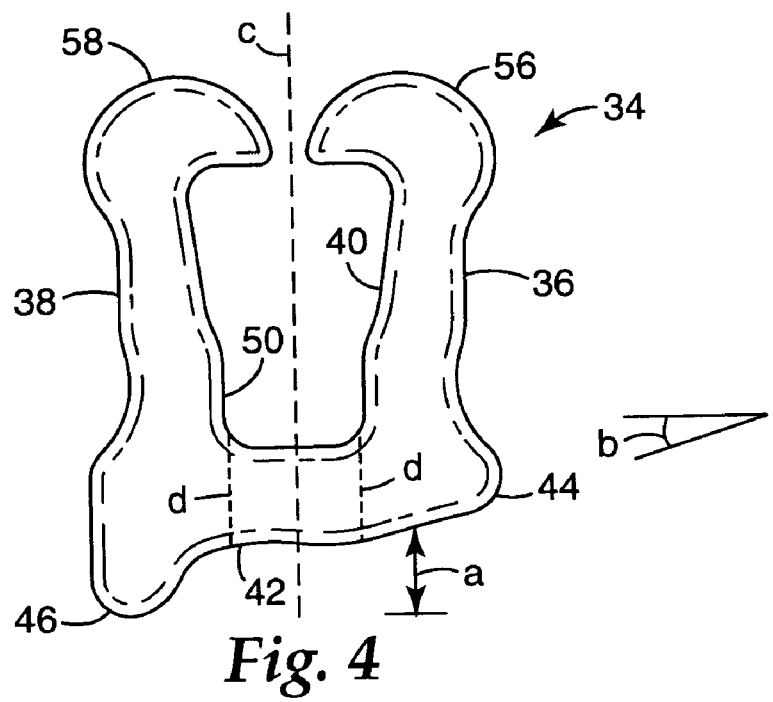
FIG. 4 is an enlarged side elevational view of one of two clips that comprise a latch of the appliance depicted in FIGS. 1-3, looking at the clip alone in a mesial direction and showing the clip in its relaxed configuration.

The distal clip 34 is shown alone in FIG. 4 and has an overall, generally "C"-shaped configuration. The distal clip 34 includes a first elongated occlusal section 36 and a second elongated gingival section 38. The first section 36 and the second section 38 extend in generally parallel directions and are spaced apart from each other to present a region 40 for receiving an archwire.

The clip 34 also includes a third section 42 that has a longitudinal axis. The longitudinal axis of the third section 42 extends in a direction generally perpendicular to the direction of extension (and longitudinal axes) of the first section 36 and the second section 38. The third section 42 includes a lingual edge adjacent the base 12 and a buccolabial edge opposite the lingual edge. The lingual and buccolabial edges extend in generally parallel directions along respective occlusal-gingival reference axes.

The clip 34 also includes a first corner portion 44 that interconnects the first section 36 and the third section 42. In addition, the clip 34 includes a second corner portion 46 that interconnects the second section 38 and the third section 42. The first corner portion 44 extends in a lingual direction away from the first section 36 a certain distance, and the second corner portion 46 extends in a lingual direction away from the second section 38 a distance that is greater than such certain distance. For exemplary purposes, this distance is represented by the letter "a" in FIG. 4.

The corner portions 44, 46 contact a wall section 48 of the base 12. In this embodiment, the wall section 48 faces in a generally buccolabial direction, and is opposite the tooth-facing lingual surface of the base 12. Moreover, the wall section 48 extends in a reference plane that is oriented at an acute angle with respect to a reference plane containing the lingual side of the archwire slot 20. This angle is designated by the letter "b" in FIG. 4, and is representative of the "torque value" of the appliance 10.

The clip 34 also includes a recess 50 that is communication with the archwire-receiving region 40. The recess 50 is adapted to complementally receive the neck 26 of the distal support 24, but has an overall shape that is somewhat smaller than the overall shape of the head 28 of the distal support 24. As such, the head 28, in combination with the wall section 48, function to retain the clip 34 in coupled relation to the body 14.

The third section 42 of the clip 34 has a configuration that is generally symmetrical about a reference axis perpendicular to the longitudinal axis of the third section 42 when viewed in a "clip" reference plane containing the first section 36, the second section 38 and the third section 42. As shown in FIG. 4, the first section includes an inner edge that is next to the third section and extends along a first reference plane and the second section includes an inner edge that is next to the third section and extends along a second reference plane, wherein the first plane and second plane are generally parallel to each other when the clip is relaxed. In the region between the first section 36 and the second section 38, the third section 42 has a configuration that is generally symmetrical about a median plane, wherein the median plane is parallel to and equidistant from the first and second planes when the clip is relaxed. In FIG. 4, an exemplary reference axis is designated by the letter "c". For exemplary purposes, the third section 42 in FIG. 4 lies beneath the recess 50 in a lingual direction and, in this example, is bounded by the dashed lines "d", "d".

The clip 34 also has a pair of arm portions 56, 58 that extend inwardly toward each other. The arm portion 56 is integrally connected to a buccolabial end of the first section 36, and the arm portion 58 is connected to a buccolabial end of the second section 38. An outer buccolabial edge of the arm portions 56, 58 is smoothly curved in an arc about a mesial-distal reference axis.

Figure 5:
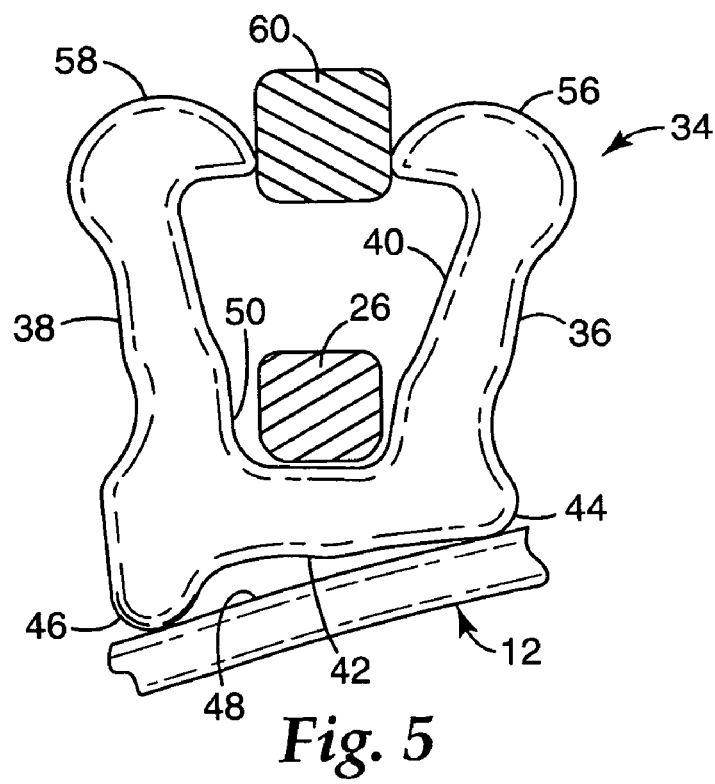
FIG. 5 is a side elevational view in partial cross-section of the clip shown in FIG. 4 along with a portion of the appliance shown in FIGS. 1-3, additionally illustrating for exemplary purposes an archwire being inserted into an archwire-receiving region of the clip.

The clip 34 is shown in its normal, relaxed configuration in FIGS. 1-4. However, the arm portions 56, 58 are movable away from each other in order to admit an archwire into the archwire-receiving region 40 when desired. To this end, the first and second sections 36, 38 bend in respective arcs away from each other in order to enable the arm portions 56, 58 to move apart from each other. FIG. 5 is an exemplary illustration showing the clip 34 as it might appear during insertion of an archwire 60 into the archwire-receiving region 40.

The smooth, curved outer edges of the arm portions 56, 58 enable the clip 34 to open and admit an archwire into the region 40 by pressing the archwire against the outer curved edges of the arm portions 56, 58. As pressure is exerted on the curved edges by the archwire, the first and second sections 36, 38 deflect away from each other in order to admit the archwire into the region 40. Once the archwire is received in the region 40, the inherent resiliency of the clip 34, and particularly the resiliency of the first and second sections 36, 38, enables the arm portions 56, 58 to spring back toward each other and to their normal, relaxed configuration as shown in FIGS. 1-4 in order to retain the archwire in the archwire slot 20.

The clip 34 (including the first and second sections 36, 38) is sufficiently stiff to retain the archwire in the archwire slot 20 during the course of orthodontic treatment so long as the force is exerted by the archwire on the appliance 10 are below a certain minimum value in a generally buccolabial direction (more particularly, in a direction opposite to the direction of insertion of the archwire into the archwire slot 20). However, whenever the forces exerted by the archwire on the appliance 10 in the same direction are greater than the minimum value, as might occur when unexpectedly high forces are encountered, the first and second sections 36, 38 deflect outwardly and the arm portions 56, 58 move apart from each other to open the clip 34 and enable the archwire to be released from the archwire slot 20. Further details regarding such forces are described in the aforementioned PCT applications entitled "ORTHODONTIC APPLIANCE WITH SELF-RELEASING LATCH", WO01/22901 and WO02/089693.

Preferably, the mesial clip 32 is identical to the distal clip 34. The latch 30, comprising the clips 32, 34, preferably releases the archwire from the archwire slot 20 in a generally buccolabial direction whenever the archwire exerts a force in the same direction on the appliance 10 that is in the range of about 0.2 lb (0.1 kg) to about 11 lb (5 kg), more preferably in the range of about 0.4 lb (0.2 kg) to about 5.5 lb (2.5 kg), and most preferably in the range of about 0.75 lb (0.34 kg) to about 3.0 lb (1.4 kg). Preferably, the minimum value is sufficiently high to prevent the archwire from unintentionally releasing from the archwire slot 20 during the normal course of orthodontic treatment. As such, the archwire can exert forces on the appliance 10 sufficient to carry out the treatment program and move the associated tooth as desired.

Preferably, the minimum value for self-release (i.e., self-opening) of the latch 30 is substantially less than the force required in the same direction to debond the appliance 10 from the associated tooth. The minimum value for self-release of the latch 30 is preferably less than about one-half of the force required in the same direction to debond the appliance 10 from the associated tooth. For example, if the expected bond strength of the adhesive bond between the appliance 10 and the associated tooth is 16 lbs (7.2 kg) in a buccolabial direction, the latch 30 is constructed to self-release the archwire whenever the archwire exerts a force in the same buccolabial direction on the appliance 10 that is somewhat greater than about 8 lbs (3.6 kg).

To determine the force to release the latch 30, a section of archwire is selected having an area in longitudinally transverse sections that is complemental to (i.e., substantially fills) the cross-sectional area of the archwire slot 20. Next, a sling is constructed and is connected to the archwire section at locations closely adjacent, but not in contact with the heads 28 of the supports 22, 24. Optionally, the sling is welded or brazed to the archwire section. Next, the sling is pulled away from the appliance 10 while the appliance 10 is held in a stationary position, taking care to ensure that the longitudinal axis of the archwire section does not tip relative to the longitudinal axis of the archwire slot 20. The force to release the latch 30 may be determined by use of an Instron testing apparatus connected to the sling, using a crosshead speed of 0.5 in/min (1.3 cm/min). Alternatively, a shaker apparatus (such as Model 300 from APS Dynamics of Carlsbad, Calif.) may be used along with a force transducer (such as model 208C01 from PCB of Buffalo, N.Y.) to measure the force.

Preferably, the distance between the opposed ends of the arm portions 56, 58 is less than the overall occlusal-gingival dimension of the smallest archwire expected to be used during the course of treatment. The archwire need not fill the archwire slot 20 and flatly engage the wall portions defining the archwire slot 20 in all instances. For example, a somewhat smaller wire, and perhaps an archwire having a circular cross-sectional shape, may be used during a portion of the treatment program. The distance between the opposed ends of the arm portions 56, 58 is preferably selected so that a variety of archwires of different cross-sectional configurations may be used in connection with the appliance 10.

As mentioned above, the distal clip 34 is preferably identical to the mesial clip 32. Optionally, however, it is possible to construct the clips 32, 34 somewhat differently to address certain circumstances. For example, if a malpositioned tooth is initially oriented such that its mesial side is rotated in a lingual direction, it may be desirable to increase the stiffness of the mesial clip 32 so that a somewhat greater force is needed to release the archwire from the archwire slot 20 in comparison to the force needed to release the archwire from the distal clip 34. Other options are also possible.

Optionally, the spring clips 32, 34 are cut from a flat section of metallic stock material. Suitable metallic materials include shape memory alloys such as alloys of nitinol and beta-titanium. The clips 32, 34 may be cut from the stock material using a stamping, die cutting, chemical etching, EDM (electrical discharge machining), laser cutting or water jet cutting process. As another option, the clips 32, 34 could be formed and then heat treated to set their shapes.

As presently preferred, the clips 32, 34 are made from flat annealed superelastic material (such as nitinol) having a pickled surface. Preferred nitinol materials have a nickel content of 55.97% by weight $A_f$ of $10°±5°$ C. The nitinol is cold worked to 37.5% and has a thickness in the range of about 0.012 in. (0.3 mm) to about 0.016 in. (0.4 mm). The clips 32, 34 are first cut in a rough cutting EDM process, then cut along their edges for an additional one or more times using an EDM process in order to smooth the edges. Alternatively, a laser cutting process or chemical etching process could be used to make the clips 32, 34. Preferably, the clips 32, 34 are constructed so that the longitudinal direction of the clip material, or the principal direction of grain flow of the clip material, is substantially parallel to the direction of extension of the first and second sections 36, 38 (i.e. a generally buccolabial direction).

Subsequent to the EDM, laser cutting or chemical etching process, the clips 32, 34 are tumbled in order to further round their edges. An example of a suitable tumbling machine is model LC-600-2+2 from Richwood Industries. Using a small barrel, and a machine speed of 200 rpm, the clips are tumbled for about 2 hours in 500 cc of water and tumbling media. An example of suitable tumbling media is a mixture of 500 cc of ceramic media (shaped ACC, type M, size 3/16×3/8(4.7 mm×9.5 mm), 25 cc of white alumina powder no. 40, and 25 cc of soap powder compound no. 43, all from Richwood Industries. The tumbled clips are then polished for one-half hour in an ultrasonic screen barrel in a tank of solution. An example of a suitable solution is 3 liters of deionized water, 3 liters of pickling solution and 0.6 liter of hydrogen peroxide. A suitable pickling solution is No. TI121 Pickling Solution from Aya International of Los Angeles, Calif.

The body 14 may be made by any suitable manufacturing process such as machining or injection molding (including metal injection molding). Preferably, the tumbling and heat treating operations are carried out after the body 14 is fabricated. Suitable materials for the body 14 include stainless steel nos. 17-4 PH, although other materials are also possible. Examples of such other materials include other alloys of stainless steel or other metallic materials, ceramic materials (including monocrystalline and polycrystalline light-transmitting ceramics such as described in the references cited above) and plastic materials (such as fiber-reinforced polycarbonate).

To assemble the clip 34 to remaining components of the appliance 10, the clip 34 is preferably put in place before the base 12 is affixed to the body 14. During assembly, the clip 34 is moved in a buccolabial direction in the space between the distal head 28 and the remaining portions of the body 14 and the arm portions 56, 58 are spread apart a distance sufficient to enable the neck 26 to be received in the region 40. The clip 34 is then moved further in a buccolabial direction until such time as the neck 26 is received in the recess 50.

Next, and after the clip 32 is installed in a similar manner, the base 12 is affixed to the body 14 by a suitable process such as brazing or welding (including laser welding). Once the base 12 is affixed to the body 14, the clip 34, and particularly the third section 42, is captured between the neck 26 and the wall section 48 of the base 12 and is thereafter retained in place. At this time, the region 40 is aligned with the archwire slot 30 as can be appreciated by a comparison of FIG. 1 and FIG. 3.

Advantageously, the symmetrical construction of the third section 42, with its essentially uniform width in directions along a buccolabial-lingual reference axis at various points along its length, helps to distribute the strain and stress in the third section 42 more uniformly along its length. As a result, the maximum strain in the third section 42 during opening movements of the clip 34 is reduced. Consequently, the fatigue life of the clip 34 is enhanced and the clip 34 is less likely to fracture during use.

In the embodiment depicted in the drawings, the first section 36, the second section 38 and the third section 42 have a cross-sectional configuration that is generally rectangular. As another option, the cross-sectional shape of the sections 36, 38, 42 may resemble a rhomboid or parallelogram having no right angles. Such construction is a particular advantage when used in combination with appliances known as "angulated" appliances having an archwire slot that extends at a similar angle relative to mesial and distal sides of tiewings and/or the appliance body. In these instances, the total area occupied by a clip may remain the same without unduly decreasing its cross-sectional area or its resultant strength and fatigue life. Examples of such construction are described in published U.S. patent application Ser. no. 2004/0086825.

All of the patents and patent applications mentioned above are expressly incorporated herein by reference. In addition, the examples described above and shown in the drawings are intended to exemplify the various aspects and benefits of the invention. However, those skilled in the art may recognize that a number of variations and additions to the appliances described above may be made without departing from the spirit of the invention. Accordingly, the present invention should not be deemed limited to the specific embodiments set out above in detail, but instead only by a fair scope of the claims that follow along with their equivalents.

The invention claimed is:

1. A clip for releasably retaining an archwire in an archwire slot of an orthodontic appliance, the clip comprising:
   a first section;
   a second section opposed to the first section, the first section and the second section extending in generally parallel directions and being spaced apart from each other to present a region for receiving an archwire;
   a third section having a longitudinal axis extending in a direction generally perpendicular to the direction of extension of the first section and the second section;
   a first corner portion interconnecting the first section and the third section; and
   a second corner portion interconnecting the second section and the third section, wherein the first corner portion extends in a direction away from the first section a certain distance, wherein the second corner portion extends in a direction away from the second section a distance that is greater than the certain distance, wherein the first section includes an inner edge that is next to the third section and extends along a first reference plane and the second section includes an inner edge that is next to the third section and extends along a second reference plane, wherein the first plane and second plane are generally parallel to each other when the clip is relaxed, wherein the third section in the region between the first section and the second section has a configuration that is generally symmetrical about a median plane, wherein the median plane is parallel to and equidistant from the first and second planes when the clip is relaxed and wherein the third section includes a buccolabial edge and a lingual edge that extend in generally parallel directions.

2. A clip for releasably retaining an archwire in an archwire slot of an orthodontic appliance according to claim 1 wherein the clip is made from a shape memory material having superelastic properties.

3. A clip for releasably retaining an archwire in an archwire slot of an orthodontic appliance according to claim 1 wherein the first section and the second section present essentially mirror images.

4. A clip for releasably retaining an archwire in an archwire slot of an orthodontic appliance according to claim 1 wherein the clip further includes a first arm portion connected to the first section and a second arm portion connected to the second section, wherein the first arm portion and the second arm portion include curved outer edges.

5. A clip for releasably retaining an archwire in an archwire slot of an orthodontic appliance according to claim 1 wherein the clip further includes a recess adjacent the third section for receiving a support.

6. A clip for releasably retaining an archwire in an archwire slot of an orthodontic appliance according to claim 5 wherein the recess is in communication with the archwire-receiving region.

7. An orthodontic appliance comprising:
   a base;
   a body extending outwardly from the base and having a wall section extending in a direction generally along a mesial-distal reference axis;
   an archwire slot extending across the body in a generally mesial-distal direction; and
   a clip for releasably retaining an archwire in the archwire slot, the clip including:
      a first section;
      a second section opposed to the first section, the first section and the second section extending in generally parallel directions and being spaced apart from each other to present a region for receiving an archwire;
      a third section having a longitudinal axis extending in a direction generally perpendicular to the direction of extension of the first section and the second section;
      a first corner portion interconnecting the first section and the third section; and
      a second corner portion interconnecting the second section and the third section, wherein the first corner portion extends in a direction away from the first section a certain distance, wherein the second corner portion extends in a direction away from the second section a distance that is greater than the certain distance, wherein the first section includes an inner edge that is next to the third section and extends along a first reference plane and the second section includes an inner edge that is next to the third section and extends along a second reference plane, wherein the first plane and second plane are generally parallel to each other when the clip is relaxed, wherein the third section in the region between the first section and the second section has a configuration that is generally symmetrical about a median plane, wherein the median plane is parallel to and equidistant from the first and second planes when the clip is relaxed, wherein the first corner portion and the second corner portion are in contact with the wall section of the body, and wherein the third section includes a buccolabial edge and a lingual edge that extend in generally parallel directions.

8. An orthodontic appliance according to claim 7 and including a second clip for releasably retaining an archwire in the archwire slot.

9. An orthodontic appliance according to claim 7 wherein the clip is made from a shape memory material having superelastic properties.

10. An orthodontic appliance according to claim 7 wherein the first section and the second section present essentially mirror images.

11. An orthodontic appliance according to claim 7 wherein the clip further includes a first arm portion connected to the first section and a second arm portion connected to the second section, wherein the first arm portion and the second arm portion include curved outer edges.

12. An orthodontic appliance according to claim 7 wherein the third section has an outer edge remote from the archwire-receiving region that is spaced from the wall section.

13. An orthodontic appliance according to claim 7 wherein the clip further includes a recess adjacent the third section for receiving a support.

14. An orthodontic appliance according to claim 13 wherein the recess is in communication with the archwire-receiving region.

* * * * *